United States Patent [19]

Maher et al.

[11] Patent Number: 5,549,585
[45] Date of Patent: Aug. 27, 1996

[54] GELLING TREATMENT FOR SUCTION DRAINAGE SYSTEM

[75] Inventors: Pascal J. Maher, Donegal; Finbarr J. Filan, Sligo; Christian Shaw, Kilkenny, all of Ireland

[73] Assignee: Abbott Laboratories, Abbott Park, Ill.

[21] Appl. No.: 269,496

[22] Filed: Jul. 1, 1994

[30] Foreign Application Priority Data

Jul. 1, 1993 [IE] Ireland .................................. 930,493

[51] Int. Cl.⁶ .......................... A61M 1/00; A61M 37/00; B27C 3/16
[52] U.S. Cl. .......................... 604/317; 141/319; 141/364; 604/84; 604/319
[58] Field of Search .......................... 588/258; 422/292, 422/294; 141/319, 329, 364; 604/317, 318, 323, 403, 416, 905, 212, 84, 82, 326; 128/760; 222/543, 546, 129; 215/399, 320, 321, 306; 220/375, 212

[56] References Cited

U.S. PATENT DOCUMENTS

| | | | |
|---|---|---|---|
| 2,609,970 | 9/1952 | Blumson | 222/543 |
| 2,953,132 | 9/1960 | Richter et al. | 141/329 |
| 3,307,752 | 3/1967 | Anderson | 222/543 |
| 4,606,734 | 8/1986 | Larkin et al. | |
| 5,185,007 | 2/1993 | Middaugh et al. | 609/320 |
| 5,234,419 | 8/1993 | Bryant et al. | 604/319 |
| 5,238,582 | 8/1993 | Hori et al. | 422/292 |
| 5,419,769 | 5/1995 | Devlin et al. | 604/319 |

*Primary Examiner*—Mary Beth Jones
*Assistant Examiner*—David J. Cho

[57] ABSTRACT

A gelling system for treating waste, such as bodily fluids, comprises a sealed receptacle (20) including a lid (21) and a chamber (23) within the receptacle for receiving the waste, a waste inlet port (24) in the lid connected to the interior of the chamber (23), an outlet port (25) in the lid (21) for connection to a suction source; and a container (1) for storing waste-treating material (e.g. a gelling agent), and for dispensing the waste-treating material into the chamber (23). When the suction system is in use is the container (1) is unattached to the receptacle (20) but, when it is desired to treat waste within the chamber (23), the container (1) is freely attachable to the receptacle (20) by means of an elongate dispensing nozzle (8) on the container which connects with the waste inlet port (24) to dispense the waste-treating material into the chamber. The container (1) has a removable cap (11) which in one position fits over the nozzle (8) of the container to form a fluid-tight seal on the nozzle (8), and which, in a second position, when removed from the nozzle (8), is used to seal the outlet port (25).

1 Claim, 5 Drawing Sheets

GELLING TREATMENT FOR SUCTION DRAINAGE SYSTEM

TECHNICAL FIELD

Suction drainage systems having a connection from a rigid container or a flexible liner to the body of a patient and a connection from the container or liner to a suction source have been widely utilized in hospitals. These systems collect waste, in the form of body fluids, from surgical and other patients in a disposable container or flexible liner having an integral lid or cover. The aspirated waste often is highly infectious and often subject to exposure caused by spills or a failure of the suction drainage system.

BACKGROUND ART

Our European Patent Application Nos. O 391 219 and O 390 095 disclose a suction drainage control system that reduces an operator's exposure to infectious waste by permitting waste-treating material to be dispersed into a sealed chamber in which the infectious waste is contained. The sealed chamber includes a cover with a flexible liner sealed to and suspended therefrom. A freely movable reservoir is provided inside the chamber for storing the waste-treating material, which reservoir is opened by manipulating the flexible liner to open the reservoir.

Our European Patent Application No. O 390 094 discloses a system in which a normally closed reservoir is provided on an underside of the cover of the chamber for storing the waste-treating material therewithin as long as the reservoir remains closed. An externally operated actuator is provided on the cover for opening the reservoir to release the waste-treating material into the sealed chamber having a flexible liner.

Our European Patent Application No. O 394 687 discloses a suction drainage system having absorbent and/or germicide to treat waste and/or locking connections and/or valves to minimize the possibility of escaping waste. A transfer system is also provided to facilitate the use of multiple containers in a single system.

U.S. Pat. No. 5,156,823 discloses a device for use in treating waste body fluids comprising a waste container for storing body fluids and body fluid solutions, an aspiration port at an upper portion of the waste container for aspirating the body fluids and body fluid solutions, a discharge port at an upper portion of the waste container, means for holding a chemical agent in an inner upper portion of the waste container, and a chemical agent comprising a coagulant for coagulating body fluids and body fluid solutions in the waste container.

In the prior art apparatus the container containing the gelling agent is permanently attached to the suction drainage system, which provides a limitation on its freedom of use. Furthermore, in systems where the gelling agent is introduced to the suction drainage system through the inlet port, as is the case in the apparatus of FIG. 1 of U.S. Pat. No. 5,156,823, difficulties are encountered in passing the gelling agent, which is usually in powder or granular form, through the port, which is relatively narrow. This is particularly so because the particles of the gelling agent tend to expand when they come into contact with moisture, which is usually present on the inside walls of the inlet port. The swollen particles then block the port preventing or restricting the entry of the remainder of the gelling agent.

OBJECT OF THE INVENTION

It is an object of the invention to provide a simple and safe suction drainage infection control system.

It is a further object of the invention to provide a suction drainage system incorporating a gelling agent, or absorbent, and/or a germicide which is contained in a container normally separate from the system but which is freely attachable to the system when it is desired to introduce the gelling agent, or absorbent, and/or germicide into the system.

It is yet a further object of the invention to overcome the problems inherent in the prior art apparatus, as discussed above.

SUMMARY OF THE INVENTION

The present invention is directed to an improved gelling treatment for a suction drainage infection control system.

More particularly, the present invention is directed to a suction drainage infection control system wherein a gelling agent, or an absorbent, and/or a germicide, (hereinafter referred to as a "waste-treating material") is released or dispensed into a disposable rigid container or flexible liner. The waste-treating material is located in an enclosed container having a nozzle which fits into an inlet port in the lid of the rigid container or flexible liner to release the waste-treating material into the container or liner.

In accordance with one aspect the invention provides a suction system for draining waste from a source, comprising a sealed receptacle including a lid and, optionally, a flexible liner defining a chamber within the receptacle for receiving the waste, a waste inlet port in said lid connected to the interior of the chamber, an outlet port in said lid for connection to a suction source; a reservoir for storing waste-treating material, and for dispensing said waste-treating material into the chamber; characterized in that the reservoir comprises a container which when the suction system is in use is unattached to the receptacle but which, when it is desired to treat waste within the chamber, is freely attachable to the receptacle by means of an elongate dispensing nozzle on the container which connects with the waste inlet port to dispense the waste-treating material into the chamber.

The container has a removable cap which in one position fits over the nozzle of the container to form a fluid-tight seal on the nozzle, and which, in a second position, when removed from the nozzle, is adapted to seal the outlet port.

In accordance with a second aspect the invention provides a container for use with the suction system, the container comprising an enclosed chamber for containing a waste-treating material, an outlet from said chamber including a dispensing nozzle which is adapted to form a fluid tight connection with the waste inlet port of the fluid receptacle so as to dispense waste-treating material from the container into the waste inlet port. The nozzle on the container forms a fluid tight fit with the waste inlet port, and provides a dry channel through which the waste-treating material may be dispensed into the chamber.

Thus, the invention provides a closed and sealed system comprising the sealed receptacle and the waste-treating material container, which when the waste fluid within the receptacle has been treated, may be disposed of as a unitary sealed system. Each suction drainage receptacle may be used alone or in series with one or more additional receptacles.

The suction drainage infection control system of the present invention minimizes the risk of exposure for hospital personnel to infectious waste by decreasing the risk of infection and spills caused by failure to cap off full or partially full waste containers, accidental cap disconnection and liner breakage.

The suction drainage infection control system of the present invention promotes the safe handling of potentially infectious suction waste by converting the waste into a solid or semi-solid state, and/or exposing the collected waste to an effective germicidal agent that is capable of killing many types of bacteria and viruses at room temperature. The germicide is effective against HIV, hepatitis B, herpes simplex 1, polio, adeno virus, and many other potentially infectious materials, and thus dramatically reduces the potential of cross-contamination between patients and minimizes the associated risk to health care workers.

Other advantages and features of the present invention will become apparent from the following detailed description, the accompanying drawings, and the appended claims.

DETAILED DESCRIPTION OF THE PREFERRED EMBODIMENT

Figure 1:
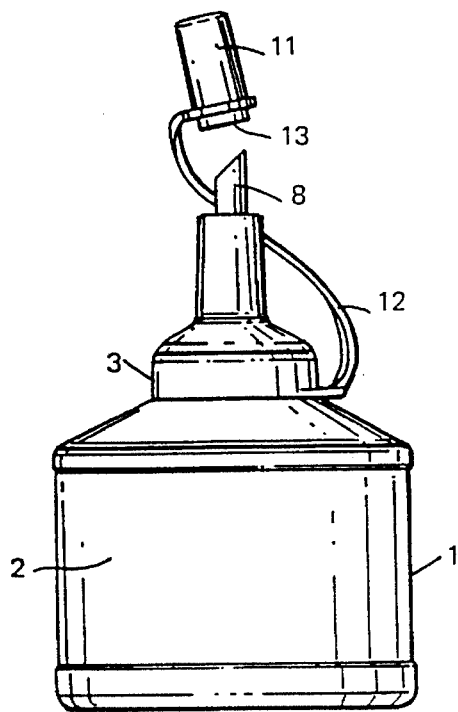
FIG. 1 is a front elevation of a container for containing waste-treating material in accordance with one aspect of the invention.

While the present invention is susceptible of embodiment in many forms, there is shown in the drawings and will hereinafter be described one presently preferred embodiment with the understanding that the present specification is to be considered as an exemplification of the invention, which is not intended to limit the invention to the specific embodiment illustrated.

Referring to the drawings, FIG. 1 is a front elevation of a container 1 for containing waste-treating material for use in the system of the invention. Preferably, the container 1 is molded from a plastics material.

Figure 2:
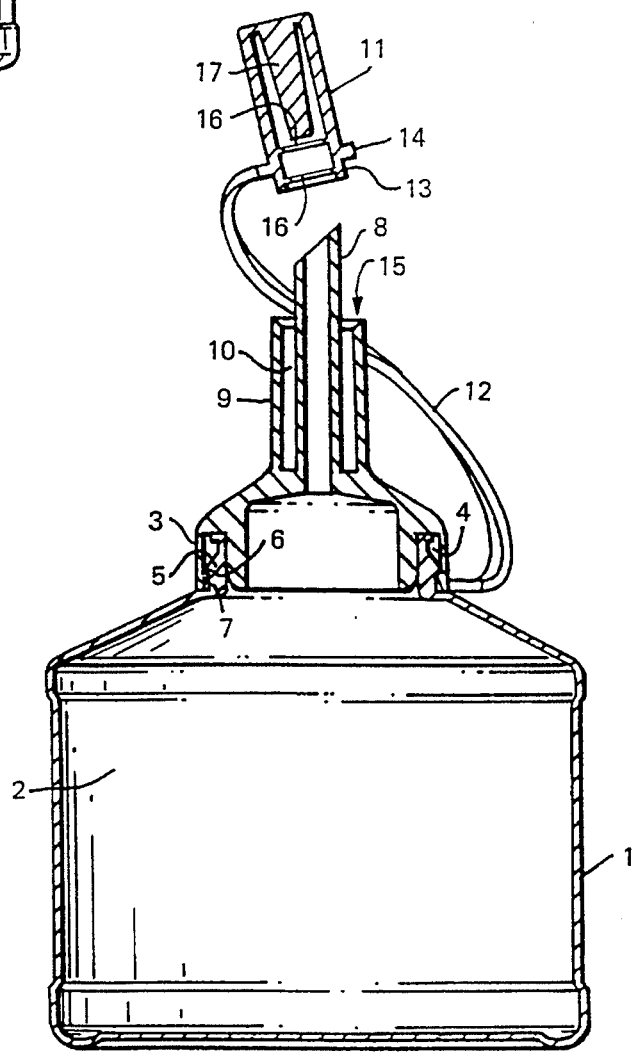
FIG. 2 is a vertical sectional view of the container of FIG. 1.

The container 1 comprises an enclosed chamber 2 for containing the waste-treating material. The container 1 has a snap-on closure 3. As shown more clearly in FIG. 2, the closure 3 has a downwardly-open annular recess 4 which fits over and accommodates an annular peripheral edge-portion 5, which defines an opening to the compartment 2. The edge portion 5 is formed with a rebate 6, which engages with a complementary recess 7 of the closure 3. When the closure 3 is fitted over the edge portion 5 of the container 1, the resilience in the material permits the rebate 6 to override the edge portion 5, such that the rebate snaps into the recess 7 to lock the closure 3 onto the container 1.

The closure 3 is formed with a dispensing nozzle 8 which is in communication with the interior of the chamber 2. The lower portion of the nozzle 8 is surrounded by a tubular sleeve 9 which defines an annular space 10 between the nozzle 8 and the sleeve 9. The free outer end of the nozzle 8 is not square, but is cut at an acute angle, preferably between 45° to 50°.

Figure 3:
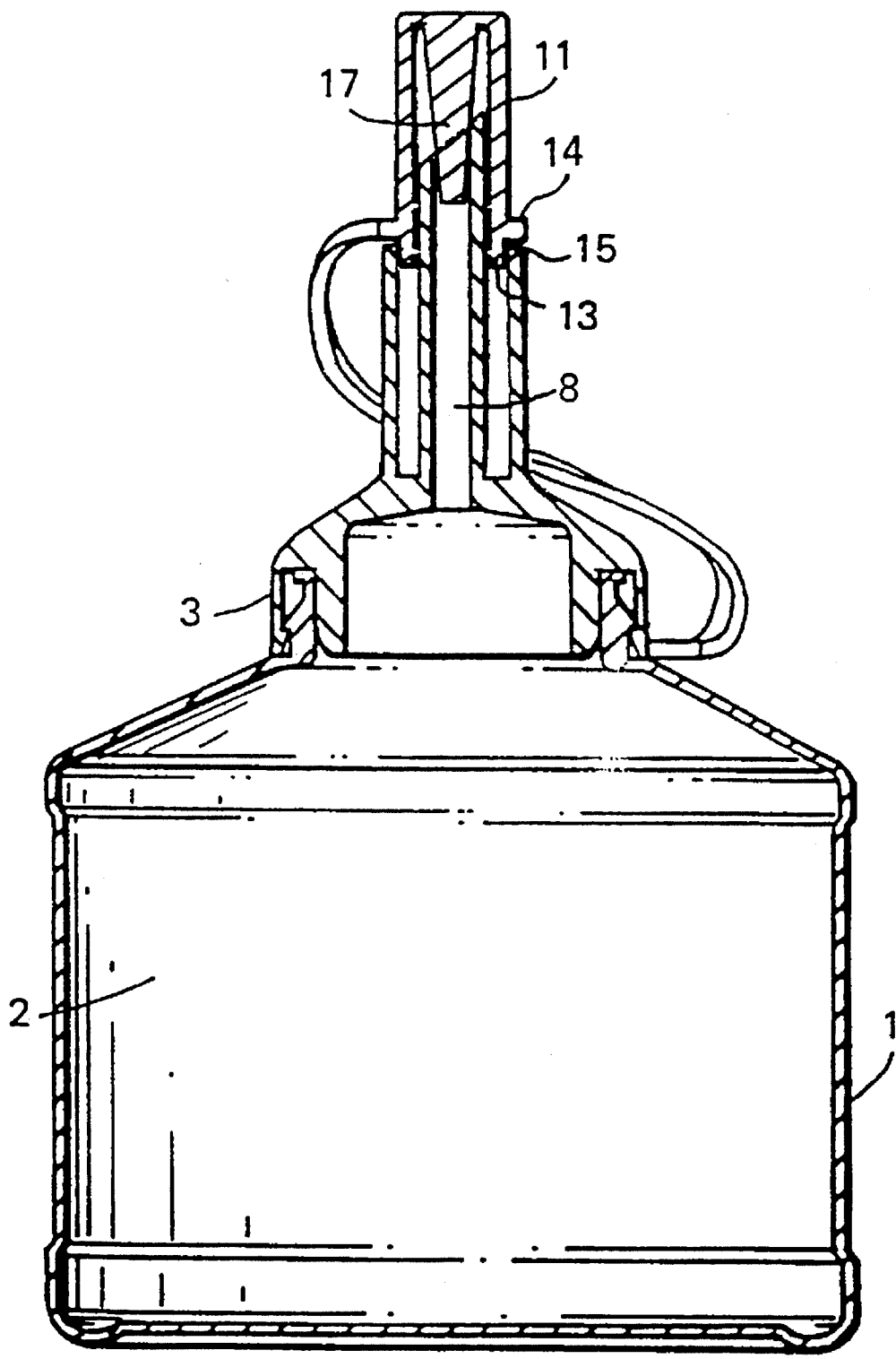
FIG. 3 is a vertical sectional view of the container of FIG. 1 in a closed state.

The container 1 is provided with a cap 11 for closing the container. The cap 11 is attached to the container 1 by means of a tag 12. As shown more clearly in FIG. 3, the cap 11 is hollow and fits over the free end of the nozzle 8. An annular end portion 13 of the cap 11 is adapted to fit into the annular space 10 between the nozzle 8 and the sleeve 9. Optionally, the inner wall of the cap 11 is provided with annular ribs 16 which provide for an interference fit between the cap 11 and the nozzle 8. An annular collar 14 on the cap abuts the top edge portion 15 of the sleeve 9. An integral plug 17, which is of frusto-conical shape, is disposed axially within the cap 11, and is adapted, when the cap 11 is placed over the end of the nozzle 8, to fit tightly within the nozzle as shown in FIG. 3. In this way a very secure and fluid-tight seal is obtained between the cap 11 and the nozzle 8.

Figure 4:
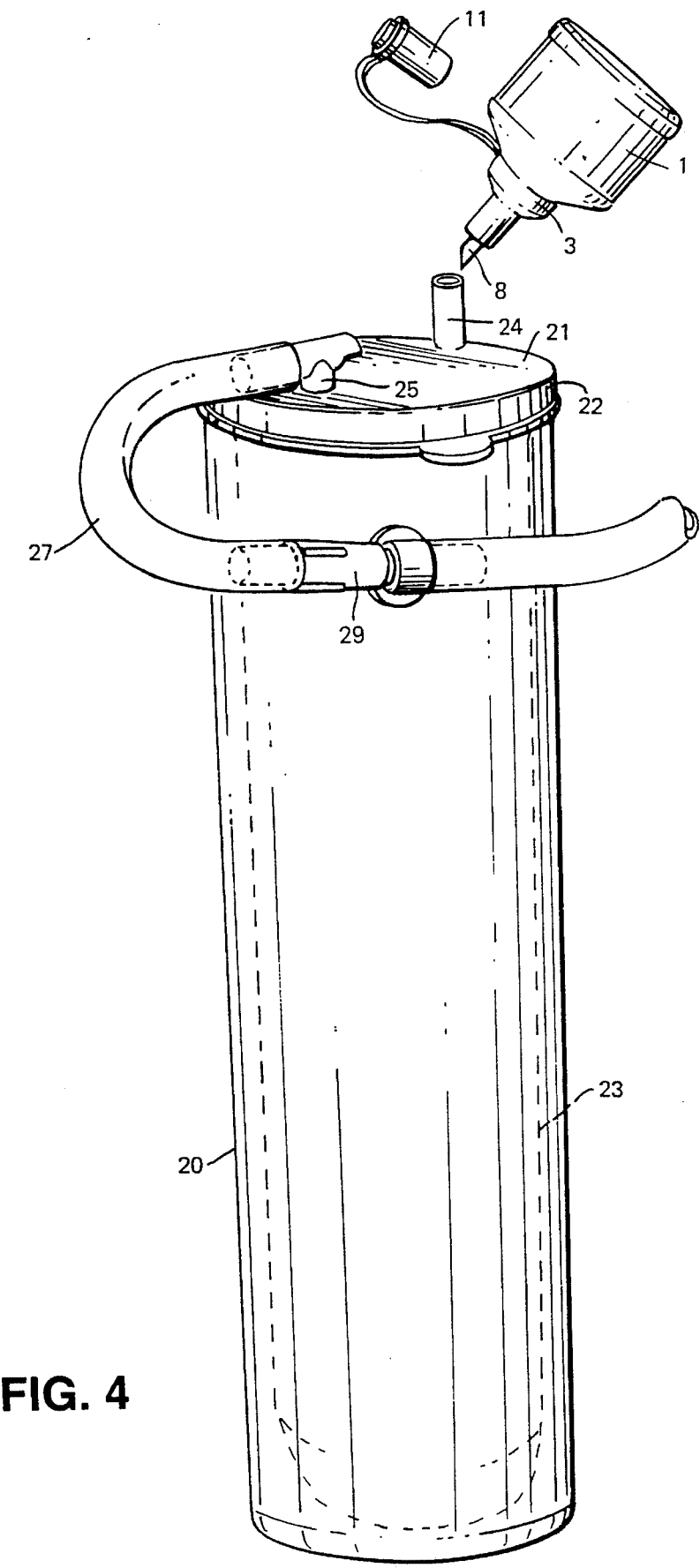
FIG. 4 is a front elevation of one embodiment of the invention showing the container of FIG. 1 about to be connected to a waste receptacle.
Figure 5:
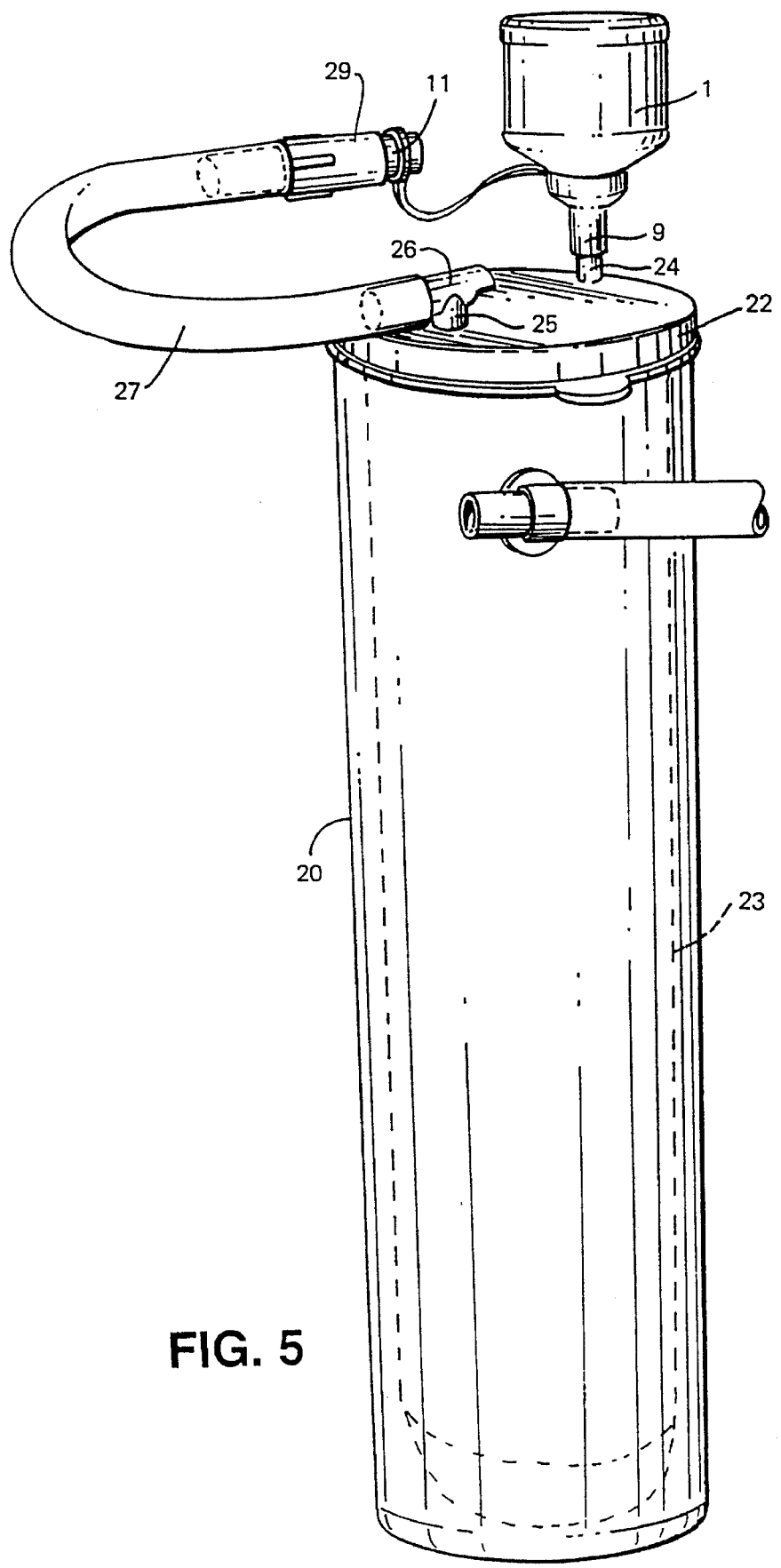
FIG. 5 is a front elevation showing the container of FIG. 1 connected to the waste receptacle.
Figure 6:
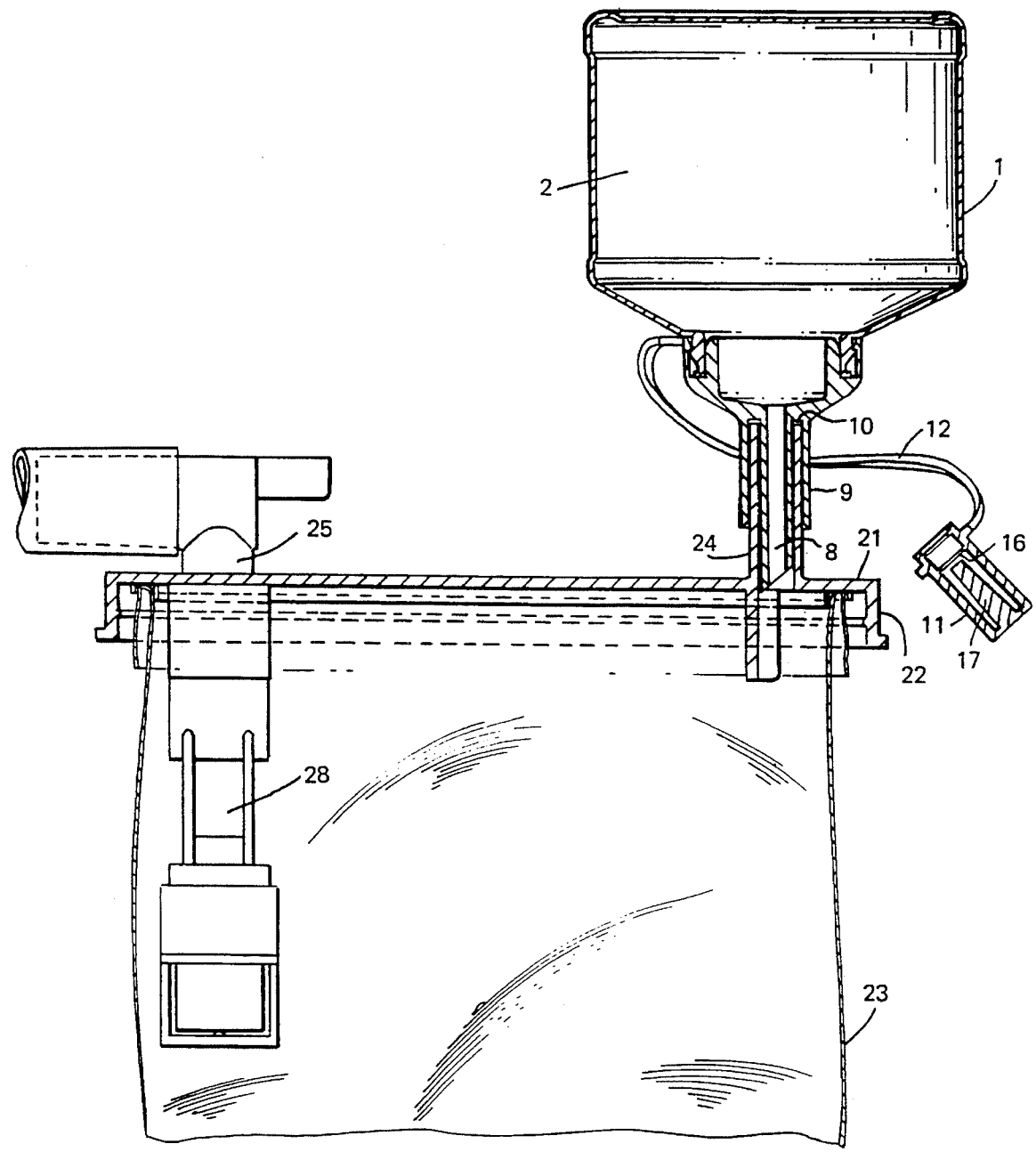
FIG. 6 is a fragmentary vertical section of a detail of FIG. 5.

An embodiment of the complete suction drainage container infection control system of the present invention is illustrated in the FIGS. 4 to 6.

In addition to the container 1, described above, the system includes a cylindrical receptacle 20 that can be constructed of a relatively rigid plastics material. The receptacle 20 is open at the top and closed at the bottom. The receptacle 20 is not contacted by the waste so it may be repeatedly used. In the unlikely event of it becoming contaminated, it may be autoclaved at a temperature of about 121° C., or may be chemically sterilized. The receptacle 20 is mounted on a metal cradle (not shown). Cradles of varying heights may be used, and may accommodate a plurality of receptacles 20.

The receptacle 20 is adapted to receive a unitary structure comprising a receptacle lid 21 having a depending flange 22 for fluid tight engagement with the upper open end of the receptacle 20. A flexible liner 23 which is fused, e.g. by RF welding, or otherwise secured, to the underside of the lid 21 in a completely fluid tight manner. The liner 23 is in the form of a fluid-tight bag which is adapted to receive and contain the waste liquid. Preferably, the liner is a strong flexible unitary container. It may be blow-molded from a plastics material, such as polyvinyl chloride, so as to eliminate weak areas, such as seams.

The lid 21 includes an inlet port 24 and an outlet port 25, both of which open into the interior of the liner 23. The inlet port 24 is comprised of an upwardly extending tubular portion on the outside of the lid 21, and a downwardly extending tubular portion on the underside of the lid 21. The upper end of the inlet port 24 is adapted for connection to an inlet tube or line (not shown) and is connected to the source from which fluid is to be drained. For example, it may be connected to a patient by means of a catheter.

The other end of the inlet port 24 depends beneath the lid 21 and in is communication with the interior of the liner 23. Though not shown in the drawings, a valve may be provided in series with the depending inner portion of the inlet port 24. The valve allows for one-way flow of waste from the source to be drained to the interior of the sealed liner 23. Suitable valves are disclosed in European Patent Applications Nos. 0 390 094, 0 394 687, and 0 390 095, the contents of which are incorporated herein by way of reference. Other suitable valves are disclosed in U.S. Pat. Nos. 3,822,720 and 3,901,272 the contents of which are also incorporated herein by way of reference.

The outlet port 25 is also provided with an upstanding tubular portion on the exterior of the lid 21, which connects by means of an elbow junction 26 to an outlet tube 27. The outlet tube 27 connects the interior of the liner 23 to a negative pressure or vacuum source (not shown) which causes the waste to be drawn into the liner 23 through the inlet port 24.

The outlet port 25 has a tubular portion which depends downwardly beneath the lid 21 into the interior of the liner 23. This tubular portion of the outlet port contains a valve 28 which prevents overflow of waste liquid into the outlet tube 27. The valve 28 may be a mechanical valve which prevents flow of waste material through the outlet tube when the liner 23 is full, comprising a float in a housing which rises with the fluid level to block the outlet port 25 and to shut-off the vacuum. Alternatively, the valve 28 may be a non-mechanical valve comprising a housing that contains a polyethylene foam containing swellable moisture-sensitive beads made of polymers or other suitable materials. The beads swell instantly on contact with liquid to seal the outlet port 25. They also provide a highly efficient aerosol filter which prevents the suction equipment from contamination by aerosol-borne bacteria and viruses. A suitable non-mechanical valve is disclosed, for example in published PCT Application No. WO87/00439.

The operation of the system of the invention is now described with reference to FIGS. 4 to 6. On the completion of aspiration of waste material, such as body fluid, or when the liner 23 is almost full of fluid, the inlet tube is disconnected from the patient, or other waste source, and the vacuum source is disconnected. Preferably, the inlet tube is flushed with a suitable germicide, and the flushed material is collected in the liner 23. The inlet tube is then disconnected from the inlet port 24.

The cap 11 is removed from the nozzle 8 of the container 1. As shown in FIG. 4, the free end of the nozzle 8 is inserted into the open end of the inlet port 24 to dispense the waste-treating material from the container 1 into the liner 23. The waste-treating material acts within minutes to gel or solidify the waste liquid within the liner 23. The position of the container 1 when the nozzle 8 is fully inserted in the port 24 is illustrated in FIG. 5, and is shown in more detail in FIG. 6o As shown in FIG. 6, the nozzle 8 fits tightly within a tubular portion of the inlet port 24. The sleeve 9 of the container 1 fits over the outer wall of the inlet port 24 so that the top tubular portion of the inlet port 24 forms a friction fit within the annular space 10 between the nozzle 8 and the sleeve 9. In this way a very secure liquid-tight seal is obtained between the container 1 and the receptacle 20.

The provision of the nozzle 8, and its configuration, is of importance in ensuring that the waste-treating material, which usually is in granular form, flows freely through the inlet port 24, which is relatively narrow. Further, the inside wall of the inlet port 24 is usually wet and, where the waste-treating material is a gelling agent, the gel particles on coming into contact with moisture on the inside wall of the inlet port would swell and block the inlet. The nozzle 8 assists in keeping the gel particles out of contact with the inner wall of the inlet port 24. The angled configuration of the free end of the nozzle 8 is of importance. If the end nozzle was square it would tend to collect moisture from the inner wall of the inlet port 24 when the nozzle is pushed into the port. However, this is avoided by the angled configuration which avoids or minimizes the collection of moisture, and if any moisture is collected it is localized on the tip of the nozzle 8.

The nozzle 8 has a relatively small bore which controls the flow of granular or particulate waste-treating material to a near optimum rate, to provide even and consistent gelling of the waste liquid as quickly as possible given the constrained aperture size of the inlet port 25.

As shown in FIG. 5, the outlet tube 27 is disconnected from the vacuum source by disconnecting a connector 29 which is positioned on the end of the tube.

As shown in FIGS. 5 and 6 the cap 11, the exterior wall of which is of cylindrical shape, is then fitted within a complementary portion of the connector 29. The cap 11 forms a tight friction fit within the connector 29 to provide fluid-tight seal. In this way the system is tightly closed and sealed to prevent exit of contaminated material. The seal system can be disposed of as a complete unit in standard disposal boxes, or other bulk disposal containers.

The waste-treating material used in the invention may comprise a gelling agent, such as sodium acrylate copolymer, which swells in the presence of water to form an absorbent gel. It may be in the form of a powder having a particle size of 100 microns to 800 microns, and a density of 0.60 to 0.70 gm/cm$^3$ at 20° C. Other suitable absorbents include cellulose fibers, crosslinked polymeric salts, diatomaceous earth, dried clay, expanded silicate particulates, ground corncobs, perlite, silica gel, shredded polypropylene microfibers, sodium/calcium borosilicate glass, starch grafted sodium polyacrylate, thermally reticulated polyether polyurethane and vermiculite.

The waste-treating material may include a germicide. Suitable germicides include calcium hypochlorite, chlorinated tirsodium phosphate, N-chlorosuccinimide, 1,3-dichloro-5,5-dimethylhydantoin, potassium dichloro-s-triazinetrione, sodium benezene-sulfonchloramide, sodium hypochlorite, sodium p-toluenesulfonchloramide, sodium dichloroisocyanurate dihydrate, sodium dichlor-s-triazinetrione, p-sulfondichlor-amidobenzoic acid, p-toluenesulfondichloramide, trichloro-isocyanuric acid, trichloromelamine, alcohols, formaldehyde, glutareldehyde, hydrogen peroxide, iodine, quaternary ammonium compounds, paraacetic acid, paraformaldehyde and phenols. Preferred germicides include 1,3-dichloro-5,5-dimethylhydantoin, potassium dichloro-s-triazinetrione, N-chlorosuccinimide, and sodium dichloroisocyanurate dihydrate.

Although the embodiment illustrated herein is directed to a suction drainage infection control system having a flexible liner, the present invention is equally applicable to a rigid container used without a liner. Thus, as used herein, the term "receptacle" is intended to include both disposable rigid containers, and canisters having disposable flexible liners.

From the foregoing, it will be apparent that numerous modifications and variations can be effected without departing from the true spirit and scope of the novel concept of the present invention. It will be appreciated that the present disclosure is intended to set forth samples of the invention which are not intended to limit the invention to the specific embodiments illustrated. The disclosure is intended to cover by the appended claims all such modifications as fall within the scope of the claims.

Where technical features mentioned in any claim are followed by reference signs, those reference signs have been included for the sole purpose of increasing the intelligibility of the claims and accordingly, such reference signs do not have any limiting effect on the scope of each element identified by way of example by such reference signs.

We claim:

1. A method of treating waste collected in a suction system comprising the steps of: providing a sealed receptacle, including a lid and a chamber within the receptacle for receiving the waste;

providing a waste inlet port in the lid connected to the interior of the chamber;

providing an outlet port in the lid for connection to a suction source;

providing a reservoir comprising a container (1);

disposing waste-treating material in the container;

providing an elongate dispensing nozzle (8) on the container providing a removable cap (11) on the container which in one position fits over the nozzle of the container to form a fluid-tight seal on the nozzle, and which, in a second position, when removed from the nozzle, is adapted to seal the outlet port;

providing that the reservoir is unattached to the receptacle when the suction system is in use;

attaching the reservoir to the receptacle when it is desired to treat waste within the chamber (23) by removing the removable cap and inserting the dispensing nozzle into the waste inlet port (24) of the receptacle; and dispensing the waste-treating material in the container of the reservoir through the nozzle into the chamber to treat the waste collected therein.

\* \* \* \* \*